US010368977B2

(12) United States Patent
Eller et al.

(10) Patent No.: US 10,368,977 B2
(45) Date of Patent: Aug. 6, 2019

(54) ENDOGRAFT WITH AT LEAST TWO BRANCH PORTIONS

(71) Applicant: Cook Medical Technologies LLC, Bloomington, IN (US)

(72) Inventors: Derek Eller, Bloomington, IN (US); Jarin Kratzberg, Lafayette, IN (US); Saylan Lukas, Indianapolis, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/982,539

(22) Filed: Dec. 29, 2015

(65) Prior Publication Data

US 2017/0181838 A1 Jun. 29, 2017

(51) Int. Cl.
*A61F 2/06* (2013.01)
*A61F 2/07* (2013.01)
(Continued)

(52) U.S. Cl.
CPC ............... *A61F 2/06* (2013.01); *A61F 2/07* (2013.01); *A61F 2/92* (2013.01); *A61F 2/962* (2013.01);
(Continued)

(58) Field of Classification Search
CPC ...... A61F 2002/061; A61F 2/064; A61F 2/06; A61F 2/07; A61F 2/068;
(Continued)

(56) References Cited

U.S. PATENT DOCUMENTS 8,394,135 B2 3/2013 Jensen et al.
8,771,336 B2 7/2014 Roeder
(Continued)

FOREIGN PATENT DOCUMENTS

EP 2 517 671 A2 10/2012
EP 2745813 A1 6/2014
(Continued)

OTHER PUBLICATIONS

European Search Report for European Application No. EP 16275180 dated May 10, 2017, 8 pages.
(Continued)

*Primary Examiner* — Paul B Prebilic
(74) *Attorney, Agent, or Firm* — Brinks Gilson & Lione

(57) ABSTRACT

The present embodiments describe an endograft having at least two branches extending from two fenestrations on the endograft body, and methods for deploying the same. In one example, the system comprises one internal branch that is relatively straight, and one external branch that is helically curved. The fenestrations may be circumferentially located on substantially the same side of the endograft main body, and distal regions of the branches may be circumferentially located on substantially opposite sides of the main body. The branches may be longitudinally non-overlapping. Connection stents may be configured to extend from the branches to provide fluid communication with peripheral vessels. Peripheral vessels may include the coronary or renal arteries. In another example, the branches are both external to the main endograft body.

16 Claims, 6 Drawing Sheets

(51) Int. Cl.
*A61F 2/962* (2013.01)
*A61F 2/92* (2013.01)

(52) U.S. Cl.
CPC ... *A61F 2002/061* (2013.01); *A61F 2002/065* (2013.01); *A61F 2002/068* (2013.01)

(58) Field of Classification Search
CPC ........ A61F 2220/0025; A61F 2250/006; A61F 2250/0063; A61F 2250/0065; A61F 2002/068
See application file for complete search history.

(56) References Cited

U.S. PATENT DOCUMENTS

| | | | |
|---|---|---|---|
| 2006/0184228 A1* | 8/2006 | Khoury | A61F 2/07 623/1.13 |
| 2006/0247761 A1 | 11/2006 | Greenberg et al. | |
| 2009/0048663 A1* | 2/2009 | Greenberg | A61F 2/07 623/1.35 |
| 2009/0306763 A1* | 12/2009 | Roeder | A61F 2/07 623/1.13 |
| 2013/0041456 A1 | 2/2013 | Greenberg | |
| 2013/0116775 A1* | 5/2013 | Roeder | A61F 2/856 623/1.35 |
| 2013/0138199 A1* | 5/2013 | Ivancev | A61F 2/82 623/1.11 |
| 2014/0180394 A1* | 6/2014 | Greenberg | A61F 2/07 623/1.15 |
| 2014/0243952 A1* | 8/2014 | Parodi | A61F 2/07 623/1.35 |
| 2015/0223925 A1 | 8/2015 | Rasmussen et al. | |
| 2015/0230916 A1* | 8/2015 | Ivancev | A61F 2/07 623/1.13 |
| 2015/0305852 A1 | 10/2015 | Hartley et al. | |
| 2018/0243076 A1* | 8/2018 | Greenberg | A61F 2/07 |

FOREIGN PATENT DOCUMENTS

| | | |
|---|---|---|
| EP | 2 749 253 A1 | 7/2014 |
| WO | WO 2006/113501 A1 | 10/2006 |
| WO | WO 2010/111666 A1 | 9/2010 |

OTHER PUBLICATIONS

Examination Report for European Application No. EP 16275180 dated Mar. 13, 2018, 7 pages.

* cited by examiner

ENDOGRAFT WITH AT LEAST TWO BRANCH PORTIONS

BACKGROUND

The present embodiments relate generally to medical devices, and more particularly, to endografts used to treat a diseased vessel or region of vessels.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. One study found that in Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurysmal, or ruptured vessels involves the use of an endoluminal prosthesis such as a stent-graft or endograft. Such a prosthesis may provide some or all of the functionality of the original, healthy vessel and/or preserve any remaining vascular integrity by replacing a length of the existing vessel wall that spans the site of vessel failure. A properly placed prosthesis excludes the diseased and/or aneurysmal portion of the vessel. For weakened or aneurysmal vessels, even a small leak ("endoleak") in or around the prosthesis may lead to the pressurization of or flow in the treated vessel which may aggravate the condition that the prosthesis was intended to treat. A prosthesis of this type can treat, for example, aneurysms of the aortic arch, thoracic aorta, abdominal aortic, iliac, or renal arteries.

In cases of aortic pathologies such as dissection or aneurysm, it is often necessary to introduce an endograft to replace or exclude the affected portion of the anatomy. Although open repair to replace a portion of the vessel may be preferable in some cases, many patients are ineligible for open surgery due to secondary issues, and require the placement of an endograft for treatment. Currently, it may be difficult to repair the aortic root through an endovascular approach, leading to poor outcomes for aortic pathologies in some patient populations.

When an aneurysm affects a main vessel, it is important to maintain flow to the peripheral vessels. The left and right coronary arteries are peripheral vessels of the aorta. If these peripheral vessels are blocked by the main vessel prosthesis, then blood circulation is impeded, and the patient can suffer. If, for example, a coronary artery is blocked by the main vessel prosthesis, the patient can experience cardiac arrest, shortness of breath, chest pain, and reduction in blood circulation. The blockage of any peripheral vessel is usually associated with unpleasant or even life-threatening symptoms.

In general, delivery and deployment devices for endoluminal prostheses may include devices for retaining and releasing the prosthesis into the body lumen. For example, such a device may include a sheath for radially retaining the prosthesis in a compressed configuration. A pusher may be provided for pushing the sheath and the prosthesis into the body lumen and for delivering the device into a desired position. To deploy the prosthesis, the sheath may be withdrawn over the pusher and the prosthesis, thereby causing the prosthesis to become exposed and to expand into the body lumen.

SUMMARY

The disclosed embodiments relate to endograft for placement in a vessel of a patient.

In one example, the endograft has a main body having a proximal end with a proximal opening, a distal end with a distal opening, and a lumen extending therebetween. The main body may have two branches, each extending from a fenestration in the main body. Each branch may have a proximal upstream region and a distal downstream region. A majority of the first branch may be external to the main body and helically curved around a partial circumference of the main body. A majority of the second branch may be internal to the main body and have a non-helical shape.

Additional features may be included. For example, the first and second branches may be longitudinally non-overlapping. The second branch may be substantially straight relative to the helical first branch. The first and second fenestrations may be circumferentially located on substantially the same side (e.g., same half or hemi-cylinder) of the main body. The distal downstream regions of the first and second branches may be on substantially opposite sides (e.g., opposite halves or opposite hemi-cylinder) of the main body. Additional features may be included, including but not limited to those disclosed herein.

In another example, the endograft has a main body having a proximal end with a proximal opening, a distal end with a distal opening, and a lumen extending therebetween. The main body may have two branches, each extending from a fenestration in the main body. As shown in FIGS. 2 and 3, branch 180 is stitched to the fenestration 182 and as shown at FIG. 4, branch 170 is stitched at fenestration 172. Each branch may have a proximal upstream (inflow) region and a distal downstream (outflow) region. The first branch may be helically curved along a partial circumference of the main body, and the second branch may have a different shape from the first branch. The first and second fenestrations may be spaced apart less than 100 degrees relative to one another around a 360 degree perimeter of the main body. The distal downstream regions of the first and second branches are between about 110 and about 250 degrees apart relative to one another around the perimeter of the main body. The distal downstream regions of the first and second branches may be on substantially opposite sides of the main body. Additional feature may be included, including but not limited to those disclosed herein.

The methods and systems disclosed herein are nonlimiting and may be applied to other vasculature or anatomy. Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally upstream to the direction of blood flow during a medical procedure, while the term "distal" refers to a direction that is generally downstream to the direction of blood flow during a medical procedure.

The embodiments described below are in connection with systems and methods for the introduction and deployment of an implantable medical device in a vessel, such as endovascular prostheses, but could also be used for deploying a range of implantable medical devices including, but not limited to, stents, occlusion devices and the like.

Figure 1:
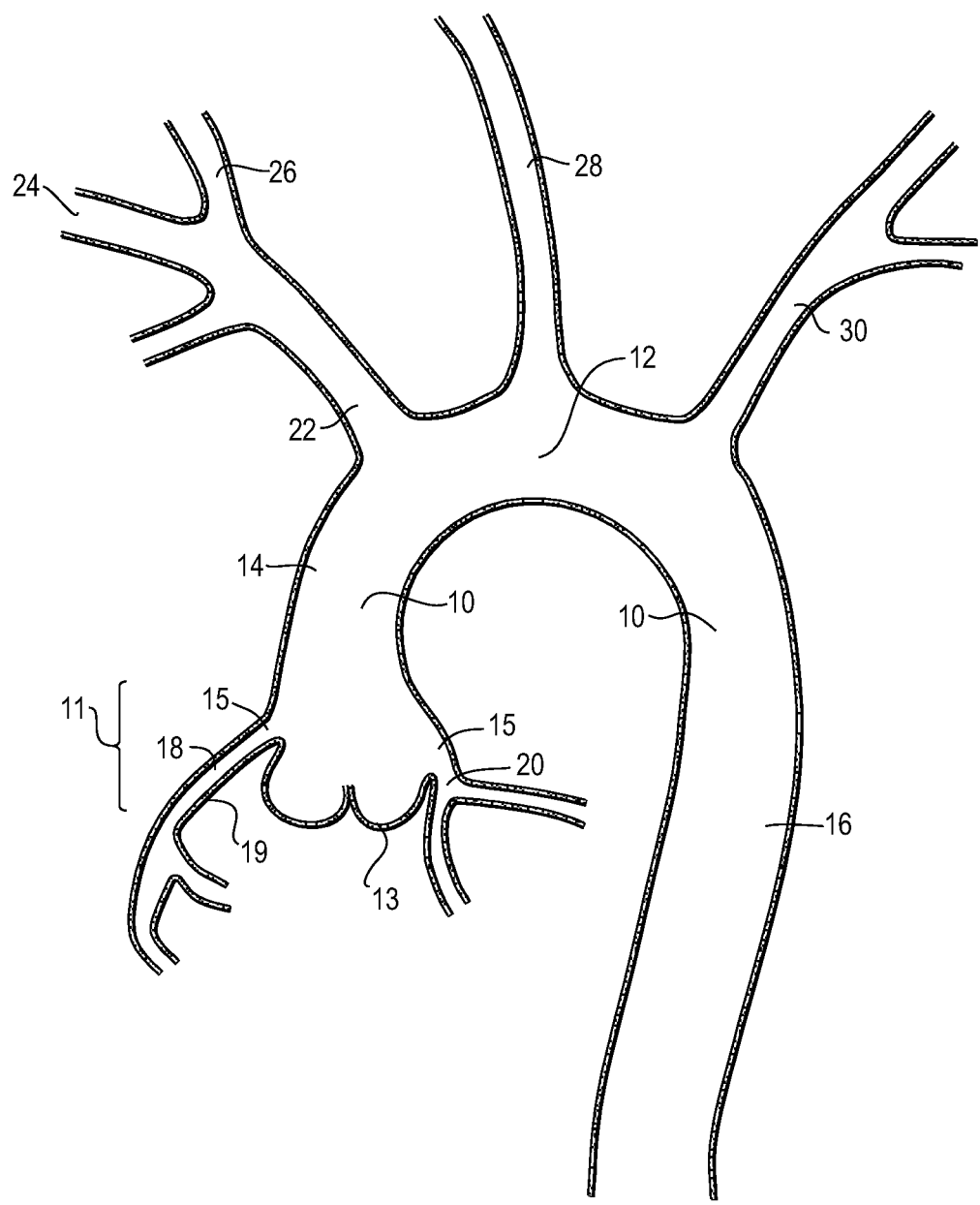
FIG. 1 is an anatomical view of the aortic root, the aortic arch, and peripheral vessels.

Referring to FIG. 1, the aorta 10 is the largest artery in the human body and carries blood away from the heart. FIG. 1 illustrates an example of an aortic arch 12, located distal to the ascending aorta 14 and proximal to the descending aorta 16. The aortic root 11 is the section of the aorta 10 closest to the heart, and includes the aortic valve 13 and coronary ostia 15. The right coronary artery 18 and left coronary artery 20 are peripheral vessels in the ascending aorta 14 and circulate blood to the heart tissue itself. Other peripheral vessels near the aortic arch 12 include the brachiocephalic artery 22, right subclavian artery 24, right common carotid artery 26, left common carotid artery 28, and left subclavian artery 30.

Over time, the walls of the aorta 10 may lose elasticity or otherwise weaken. Due to hemodynamic pressure, the vessel walls of the aorta 10 may expand in diameter, resulting in an aneurysm. While an aneurysm by itself is not an acute problem, it can increase the risk of a possibly fatal vessel rupture if the aneurysm expands and/or bursts. A common treatment for the aneurysm is to relieve the pressure on the aneurysm by redirecting blood flow through a stent graft or endograft.

Endografts may be implanted in the aorta 10, such that blood flows through the endograft, avoiding the aneurysm. Use of an endograft reduces pressure on the aneurysm and can cause the aneurysm to shrink in size. Endografts may incorporate self-expanding stents. The shape, size, and position of the endograft may also be modified through use of a balloon catheter. Aortic endovascular repair may be complicated in cases such as aortic root dilation (or dissection which originates in the aortic root or ascending aorta) by the fact that a prosthesis deployed there may block perfusion to the coronary arteries.

Figure 2:
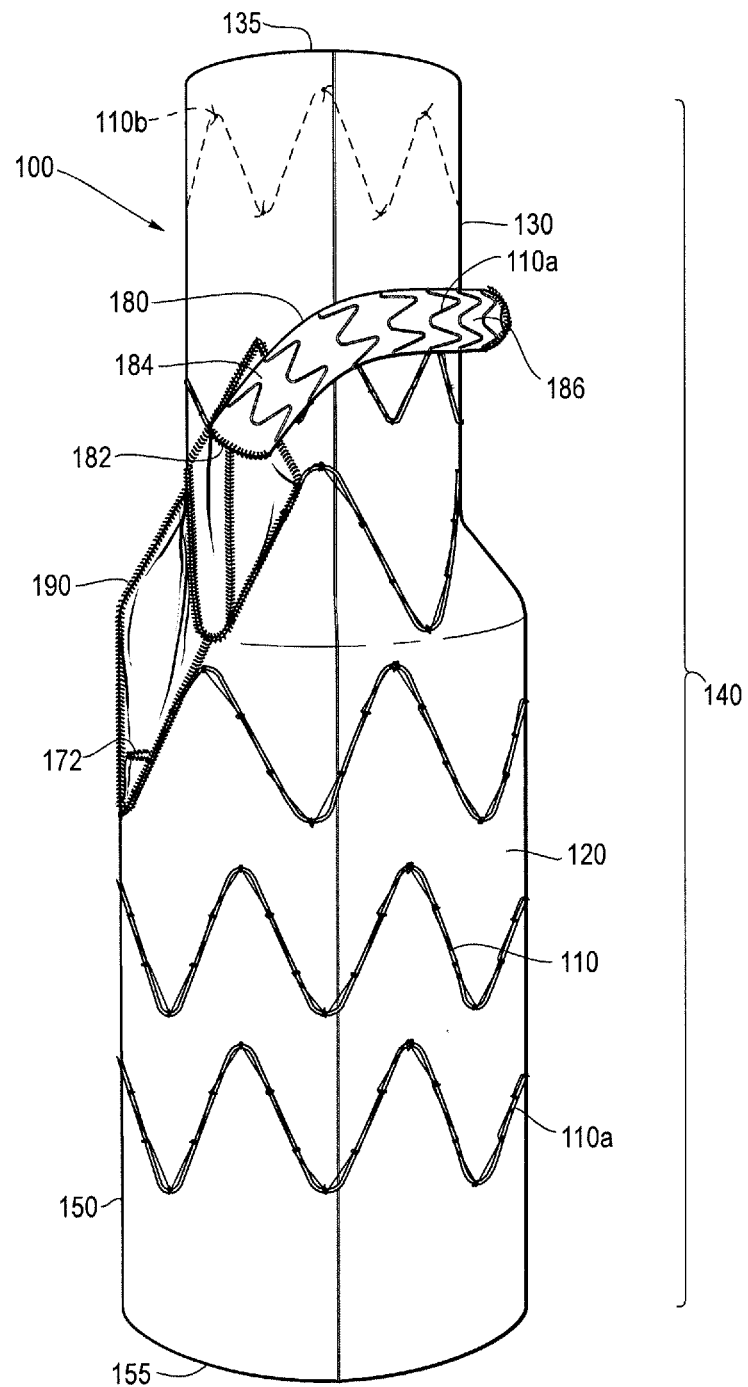
FIGS. 2-3 are side views at different angles of an embodiment of an endograft having one internal non-helical branch and one external helical branch.
Figure 3:
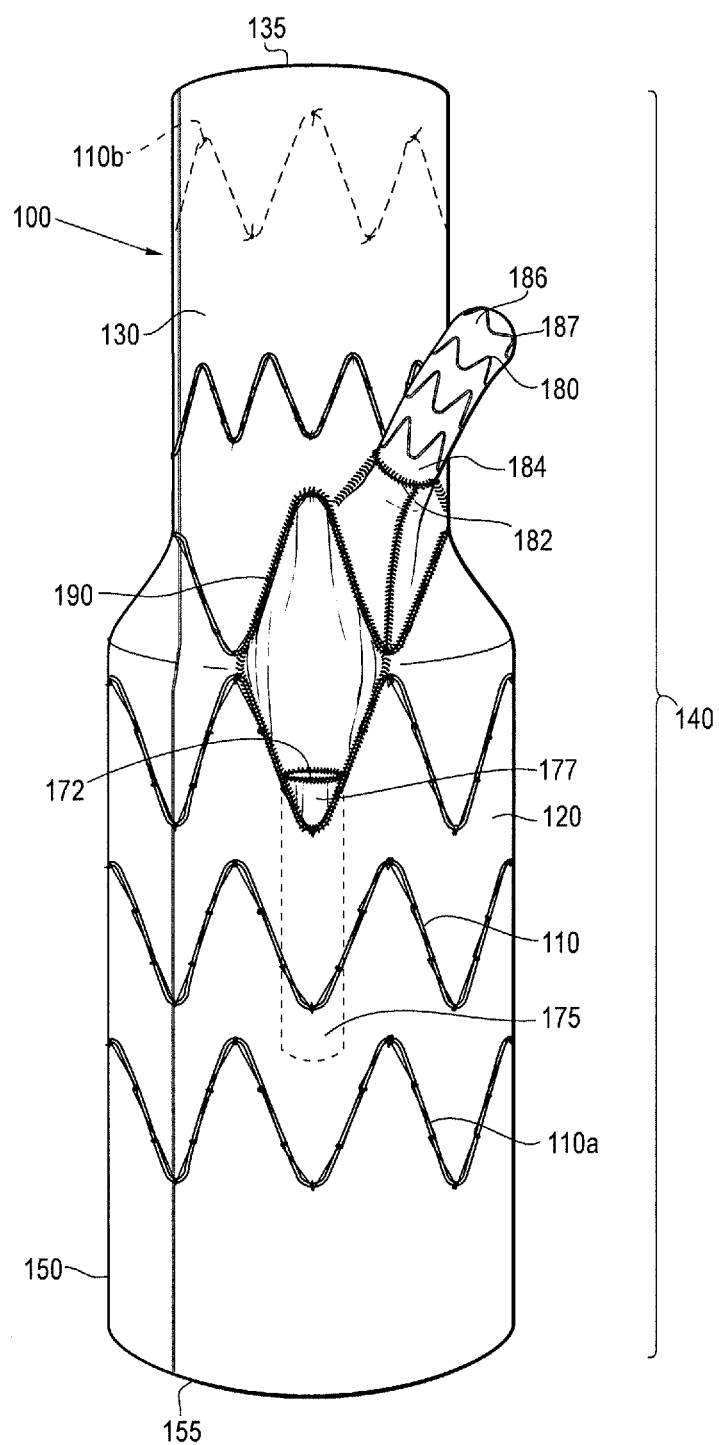
Figure 4:
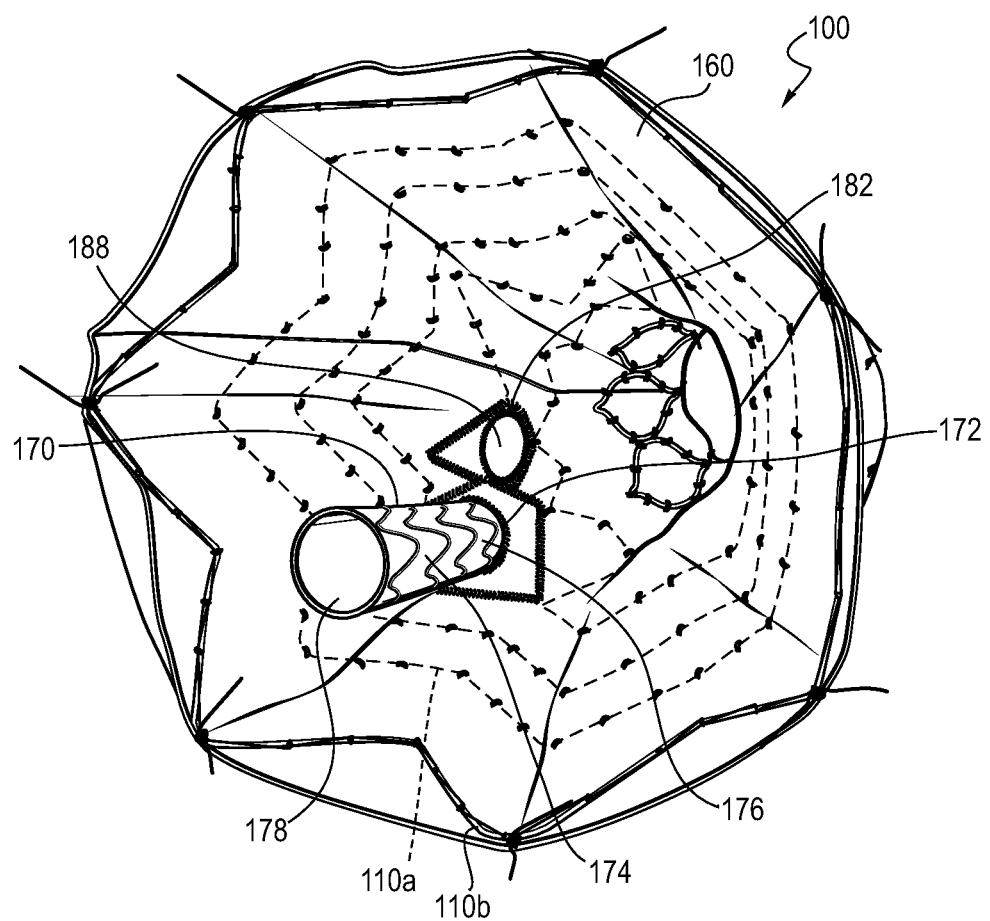
FIG. 4 is an internal view of an endograft through the distal end showing one internal branch and one external branch.
Figure 6:
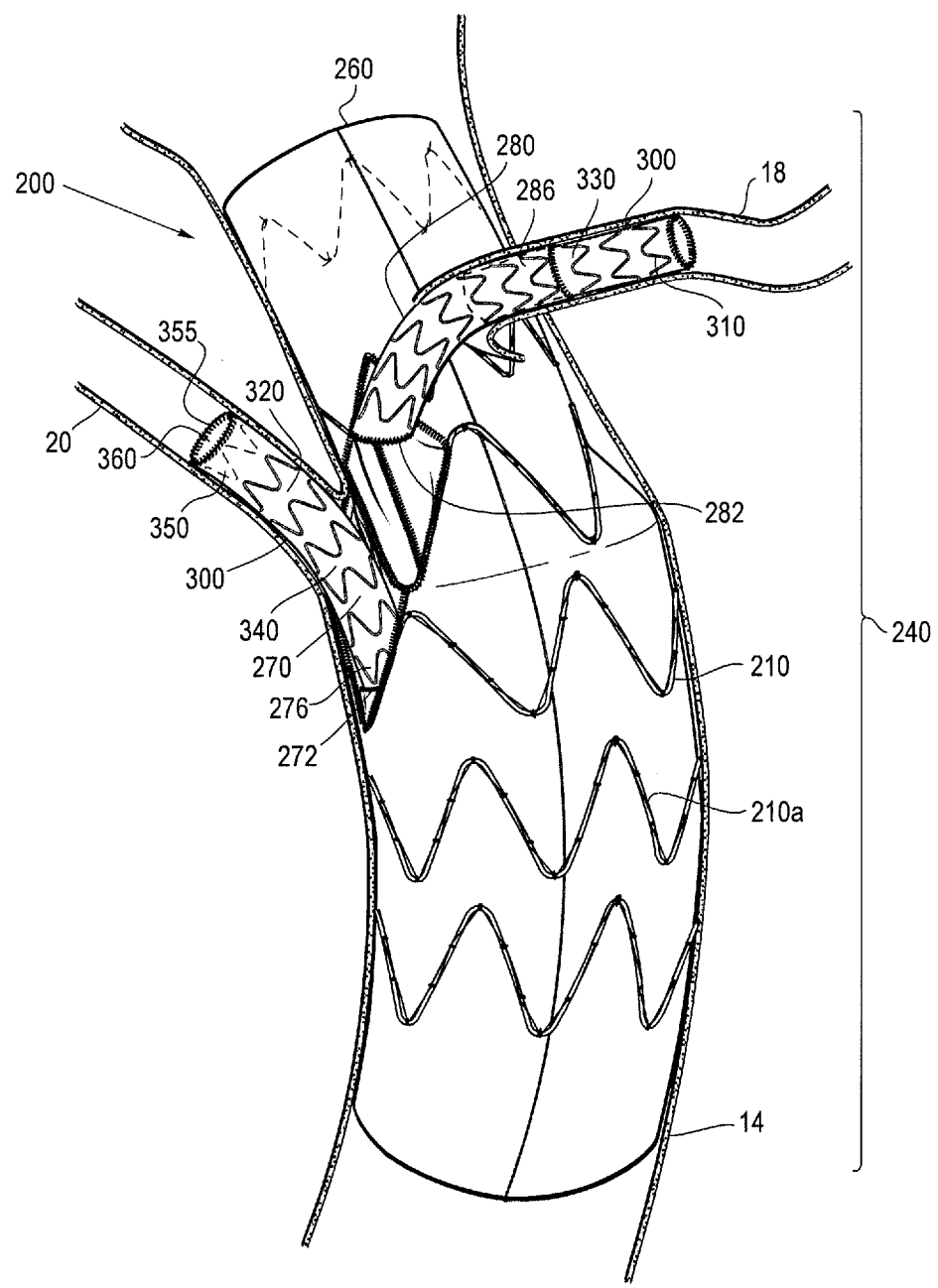
FIG. 6 is a side view of an endograft having two external branches.

FIGS. 2-4 illustrate a front view, side view, and distal end view, respectively, of an embodiment of an endograft 100. Endograft 100 comprises an expandable support structure 110 and a graft material 120, including a main body 140 having a proximal region 130, a distal region 150, and a lumen 160 extending therebetween. The proximal region 130 may have a proximal opening 135 configured as the inflow end of the endograft 100 to lie nearest the heart and the distal region 150 may have a distal opening 155 configured as the outflow end of the endograft 100 to lie furthest from the heart as shown in FIG. 6, both of which may provide fluid access to the lumen 160 of the main body 140.

The main body 140 may be generally tubular in shape, and have either a uniform or varying diameter along its length. For example, the proximal region 130 may have a smaller diameter than the distal region 150, as shown in FIGS. 2-4. The main body 140 may include a left coronary branch 170 and a right coronary branch 180, either internal or external to the main body 140, extending from a left coronary fenestration 172 and a right coronary fenestration 182, respectively. The left coronary branch 172 extends from the left coronary fenestration and toward the distal opening 155 of the endograft 100. The left coronary branch 170 may have a proximal region 174, and a first end 175, a distal region 176, and a second end 177 and a lumen 178 therebetween. The left coronary branch 170 is configured to receive blood in a retrograde fashion from its first end 175 to its second end 177 for perfusion of the left coronary artery. The right coronary branch 180 extends from the right coronary fenestration 182 and has a proximal region 184 nearest the fenestration 182, a distal region 186, and an end 187 extending away from the fenestration 182, and a lumen 188 therebetween. The right coronary branch 180 is configured to receive blood flow from the right fenestration 182 in a retrograde fashion toward the end 187 for perfusion of the right coronary artery. In this way, blood flows from the heart and through the endograft in an antegrade fashion but when in diastole (when the heart relaxes) blood flows through the left and right coronary branches in the opposite or retrograde fashion.

The support structure 110 of the endograft 100 may have any suitable stent pattern known in the art. The support structure 110 may be self-expanding or may expand under external pressures, for example from an inflatable balloon at the tip of a balloon catheter. One example of a stent pattern is the Z-stent or Gianturco stent design. Each Z-stent may include a series of substantially straight segments or struts interconnected by a series of bent segments or bends. The bent segments may include acute bends or apices. The Z-stents are arranged in a zigzag configuration in which the straight segments are set at angles relative to one another and are connected by the bent segments. Alternative stents may include, for example, annular or helical stents. The stents mentioned herein may be made from standard medical grade stainless steel. Other stents may be made from nitinol or other shape-memory materials.

As shown in FIGS. 2-4, proximal region 130, main body 140, distal region 150, left coronary branch 170 and right coronary branch 180 may each comprise at least one support structure 110, such as a stent. The support structure 110 may include a single, unitary structure or a plurality of independent structures. The support structure 110 and/or various portions thereof may be disposed on the inner surface and/or outer surface of the graft body 120. Multiple support structures 110 may be positioned at any point or points along a length of endograft 100, as generally depicted in FIGS. 2-4. In the current, non-limiting example, a plurality of external Z-stents 110a are disposed external to the graft material 120 at spaced-apart locations along the endograft 100. Internal Z-stents 110b may also be disposed along portions of the main body 140, as shown in FIGS. 2-3. Given varying design configurations, some external Z-stents 110a may be replaced with internal Z-stents 110b, and vice versa.

The graft material 120 may be connected to the one or more support structures 110 by known methods, for example biocompatible stitching 190. The graft material 120 may be fabricated from any at least substantially biocompatible material including such materials as polyester fabrics, polytetrafluoroethylene (PTFE), expanded PTFE, and other synthetic materials known to those of skill in the art. In some embodiments in accordance with the technology, the graft material 120 may also include drug-eluting coatings or implants.

When deploying the endograft 100 into the aorta 10 in the region of aortic root 11, it may be desirable to provide a left coronary branch 170 and a right coronary branch 180 to facilitate cannulation and avoid occluding the right coronary artery 18 and left coronary artery 20. The left coronary branch 170 and the right coronary branch 180 may be either internal or external to the main body 140.

In the embodiment of FIGS. 2-4, the left coronary branch 170 (shown in detail in FIG. 4) is primarily or entirely internal to the main body 140. Other embodiments may have only a majority of the left coronary branch 170 internal to the main body 140. The distal (downstream) region 176 of the left coronary branch 170 may be attached to the main body 140 at the substantially round or circular fenestration 172 in the graft material 120 of the tubular wall of the endograft 100, providing fluid communication between the lumen 160, the lumen 178, and the left coronary artery 20. As shown in FIG. 4, the left coronary branch 170 may extend from the fenestration 172 and into the lumen 160 of the endograft 100, extending distally relative to blood flow in the main body 140 (yet extending proximally relative to blood flow in the left coronary branch 170). The left coronary branch 170 may optionally be attached to the graft material 120 of the tubular wall of the main body 140. The longitudinal axis of the left coronary branch 170 may be substantially parallel to the longitudinal axis of the left coronary artery 20. This may minimize potentially turbulent blood flow from the internal left coronary branch 170 when it is fluidly coupled to the left coronary artery 20, for example through a coronary connection stent (such as connection stent 300 of FIG. 6).

Although the blood flowing through the internal left coronary branch 170 technically is moving backwards towards the heart (proximal direction), in a fluid sense (and consistent with the definitions of this application) the blood flows distally down the pressure gradient (downstream) towards the left coronary artery 20. Thus, blood flowing through the left coronary branch 170 and left coronary artery 20 generally flows anterograde (distally downstream) even as it flows towards and into the heart. This sharp "U-turn" in flow may be facilitated by brief periods of retrograde flow in the ascending aorta 14, for example, during portions of diastole. This is common in healthy individuals under normal conditions.

The right coronary branch 180 (shown in detail in FIGS. 2-3) is primarily or entirely external to the main body 140. Other embodiments may have only a majority of the right coronary branch 180 external to the main body 140. The proximal (upstream) region 184 of the right coronary branch 180 may be attached to the main body 140 at the substantially round or circular fenestration 182 in the graft material 120 of the tubular wall of the endograft 100, providing fluid communication between the lumen 160, lumen 188, and the right coronary artery 18. The fenestration 182 may be oriented in a substantially similar plane as distal opening 155, which may advantageously provide a large target surface area to facilitate cannulation. Similarly, if a portion of the proximal region 184 is internal to the main body 140, it may be oriented in a substantially similar plane as distal opening 155 to provide a large target surface area to facilitate cannulation.

As shown in FIGS. 2-3, the right coronary branch 180 may extend from the fenestration 182 in a curved helical configuration around the proximal region 130 and towards the right coronary artery 18. The longitudinal direction of helical curve may be proximal relative to blood flow in the main body 140 (yet distal relative to blood flow in the right coronary branch 180). The right coronary branch 180 may optionally be attached to the graft material 120 of the tubular wall of the main body 140. The curved helical configuration may minimize potentially turbulent blood flow from the external right coronary branch 180 to when it is fluidly coupled the right coronary artery 20, for example through a coronary connection stent (such as connection stent 300 of FIG. 6). This curved helical design also has the advantage of easing branch cannulation. A larger radius of curvature allows objects such as wires, sheaths, catheters and stents to be tracked with minimal obstructions, hang-ups, or snags. Although the blood flowing through the external right coronary branch 180 technically is moving backwards towards the heart (proximal direction) as it flows through the helical curve, in a fluid sense the blood moves distally down the pressure gradient (downstream) towards the right coronary artery 18, as described above.

The left coronary branch 170 and right coronary branch 180 may be made of a super-elastic metal frame, such as a spiral Z-stent or other self-expanding stent platform. The stent may be covered, but does not necessarily need to be, especially if located internal to the main body 140 of the endograft 100. The stents may be covered, for example, by sewing a fabric graft material 120 to the internal or external surface of the stent 110 (forming 110a or 110b), or dipping or electrospinning a polymer such as PET, PTFE, EPTFE, or a urethane material. The left coronary branch 170 and right coronary branch 180 may also be tapered such that the diameter narrows in the direction of blood flow. This may increase the ease of cannulating with a wire and stent, and/or give a more favorable flow profile into the respective branch and artery. This may also allow better stent apposition with walls. For example, the proximal portions 174 and 184 of the left and right coronary branches, respectively, could be of a larger size to facilitate cannulation, while the distal portions 176 and 186 could be of a smaller size to closely conform to stent dimensions, respectively.

The internal left coronary branch 170 and fenestration 172 may be reinforced along their perimeters to provide structural support, for example using internal or external Z-stents (not shown) or biocompatible stitching 190. Similarly, the external right coronary branch 180 and fenestration 182 may be reinforced along their perimeters to provide structural support, for example using external Z-stents 110a or internal Z-stents 110b. The fenestrations 172 and 182 may be configured to house tubular branch extensions (e.g., coronary connection stents 300, as shown in an alternative embodiment in FIG. 6) that may extend into the right coronary artery 18 and left coronary artery 20 forming a tromboning connection. As with all embodiments, radiopaque or MRI opaque markers may be used to define the periphery of the fenestrations 172 and 182. In alternative embodiments targeting other anatomy, other numbers of fenestrations may also be used.

As shown in FIGS. 2-3, the right coronary fenestration 182 and left coronary fenestration 172 may have similar circumferential orientations, for example, they may be oriented circumferentially on substantially the same side (e.g., same half or hemi-cylinder) of the tubular main body 140. In one example, the right coronary fenestration 182 and left coronary fenestration 172 may be spaced apart less than 100 degrees relative to one another around a 360 degree perimeter of the main body 140, and in particular, approximately ten to fifty degrees relative to one another. The distal downstream regions of the first and second branches are between about 110 and about 250 degrees apart relative to one another around the perimeter of the main body so that that end 187 of the first branch is spaced about 100 to 250 degrees from the ends 175 and 177. In another example, the right coronary fenestration 182 and left coronary fenestration 172 may be spaced apart approximately thirty degrees relative to one another around the 360 degree perimeter of the main body 140.

One advantage of orienting the right and left coronary fenestrations 182 and 172 circumferentially close together is that it allows the left coronary branch 170 to be generally straight and the right coronary branch 180 to be helical, such that the distal regions 186 and 176 of the right and left coronary branches, respectively, terminate on substantially opposite sides of the main body 140 and in alignment with peripheral vessels (e.g., right and left coronary arteries or renal arteries). The distal regions 186 and 176 on opposing sides (e.g., opposite halves or opposite hemi-cylinders) of the main body 140 may be approximately 180 degrees apart relative to one another around the 360 degree perimeter of the main body 140, though this is not a precise angle due to potential anatomical differences in patients. Other orientations around the entire perimeter (zero to 360 degrees) are also considered. This alignment with peripheral vessels facilitates cannulation of coronary connection stents (such as connection stent 300 of FIG. 6) since cannulation can be achieved without navigating tight turns that may be time consuming or lead to kinking and/or mechanical failure, as described in further detail below.

In use, endograft 100 may be deployed intravascularly, for example in the aortic root 11 or ascending aorta 14. The delivery system containing the graft may be tracked from a distal approach (e.g., transfemoral) and guided over the aortic arch 12. Because rotational alignment is important, the system may utilize a pre-curved cannula core to rotationally orient the system relative to the aortic arch 12, for example, embodiments of the system of U.S. Pat. No. 8,394,135. The main body 140 of the endograft 100 may be deployed by retraction of an outer sheath (not shown). The endograft 100 may employ diameter reduction ties (not shown) to prevent full deployment at this stage. The right coronary artery 18 and left coronary artery 20 may be cannulated with a catheter using standard wire and catheter techniques. After cannulation, if diameter reduction ties are in place, they may be removed to fully deploy the graft. Coronary connection stents (such as connection stent 300 of FIG. 6) may be tracked into one or both of coronary branches 170 and 180 and deployed, with a proximal end within a branch and a distal end within the respective coronary artery. After deployment wires and catheters may be removed from the system. In some embodiments, a transcatheter heart valve may be deployed into the proximal region 130 of the endograft 100, for example at the proximal opening 135.

One advantage of these systems and methods is increased ease of cannulating peripheral arteries through the main body 140 by better accommodating the angles and placement of the relevant anatomy. Deploying an aortic endograft from a transfemoral or other distal approach may be complicated by some loss of catheter and wire control caused by the great distance and curvature experienced when navigating the aortic arch for deployment. This may prove especially troublesome due to the geometry of the coronary arteries, especially if the approach requires sharp turns and/or cannulating a target with a small surface area. Cannulation is generally easier if the target has a larger surface area and if sharp turns can be avoided. The target surface area of the proximal region of a branch having a circular cross-section is greatest if the cross-section is normal to the approach angle of the cannulation device.

In most patients, the right coronary artery 18 typically extends in a nearly lateral direction relative to the longitudinal axis of the aorta 10, with an ostium located near the ventral-most position of the aortic root. This means that the origin of the right coronary artery 18 is at an approximately orthogonal angle relative to the longitudinal axis of the aorta 10 and/or the endograft 100 placed in the aorta 10. Cannulating the orthogonal right coronary artery 18 directly (without, for example, the helical wrapping of right coronary branch 180) would thus require an approximately ninety-degree turn relative to the longitudinal axis of the aorta 10. Specific problems associated with sharp turns such as an approximately ninety-degree turn may include kinking of the catheter, wire, balloon, or stent during cannulation and stent deployment, as well as mechanical failure. The present system and disclosed embodiments help prevent these issues by providing a larger radius of curvature for right coronary branch 180. This is possible because the right coronary branch 180 helically wraps around the proximal region 130 of the endograft 100 such that a distal end of the external branch is aligned with the right coronary artery 18. It will be appreciated that the right coronary branch 180 extends from a fenestration 182 having a cross-section generally normal to the angle of approach, providing a larger target angle. Another benefit may be reduced time during implantation, as a surgeon may be able to cannulate the target sites with fewer misses since the target area is larger and facing the approach angle.

In most patients, the left coronary artery 20 has a hairpin turn relative to the longitudinal axis of the aorta 10, as shown in FIG. 1, such that blood flowing into the left coronary artery 20 turns back towards the heart. The internal left coronary branch 170 may be relatively straight and aligned substantially parallel with the left coronary artery 20 (or other peripheral vessel) as well as the longitudinal axes of the aorta 10 and main body 140. Thus, when cannulating from a distal approach, the longitudinal axis of the left coronary artery 20 is substantially parallel to the longitudinal axis of an endograft 100. This facilitates cannulation since the left coronary branch 170 would be substantially parallel to the approach path through endograft, requiring only minor turns and providing a large target area for cannulation.

Overall, the present embodiments allow for deployment of an endograft having branches to cannulate peripheral vessels at challenging angles (e.g., coronary arteries) via a distal endovascular approach.

Like fenestrations 182 and 172, the proximal regions 184 and 174 of the right and left coronary branches, respectively, may also be spaced apart less than 100 degrees relative to one another around a 360 degree perimeter of the main body 140, and in particular, approximately ten to fifty degrees relative to one another. The distal downstream regions of the first and second branches are between about 110 and about 250 degrees apart relative to one another around the perimeter of the main body. The advantages outlined above with respect to orienting the right and left coronary fenestrations 182 and 172 circumferentially close together (e.g. same half or semi-cylinder) also apply to orienting the proximal regions 184 and 174 of the right and left coronary branches close together.

Another advantage of the present systems and related embodiments may be a reduced the loading profile of the endograft 100, especially if the left coronary branch 170 and right coronary branch 180 do not longitudinally overlap. As shown in FIGS. 2-4, for example, the left coronary branch 170 is primarily internal to the main body 140 and located entirely distal (relative to blood flow through the main body 140) to the right coronary branch 180, while the right coronary branch 180 is primarily external to the main body 140 and located entirely proximal (relative to blood flow through the main body 140) to the left coronary branch 170. Thus, when the endograft 100 is in a compressed delivery state, the left coronary branch 170 and right coronary branch 180 are not stacked on top of one another. This reduces the loading profile since the left coronary branch 170 and right coronary branch 180 are spaced apart on the longitudinal axis of the endograft (longitudinally non-overlapping). Additionally, even in configurations with two external branches (e.g., FIGS. 5-6), the profile may be minimized in configurations where the majority of the helical right coronary branch 280 lies proximally to the left coronary branch.

Despite the fact that the left coronary branch 170 and right coronary branch 180 may be longitudinally non-overlapping, coronary connection stents (such as coronary connection stent 300 of FIG. 6) may be used to access peripheral vessels that are at the same or similar longitudinal level (such as the coronary or renal arteries). In essence, even though the coronary branches 170 and 180 are longitudinally non-overlapping, the target peripheral vessels may be longitudinally overlapping and access by coronary connection stents. Additionally, branches 170 and 180 may facilitate cannulation of peripheral vessels on substantially opposite sides of the main vessel (such as the coronary or renal arteries), even though the fenestrations 172 and 182 are on substantially the same side of the endograft main body 140 (as shown in FIGS. 2-4).

Figure 5:
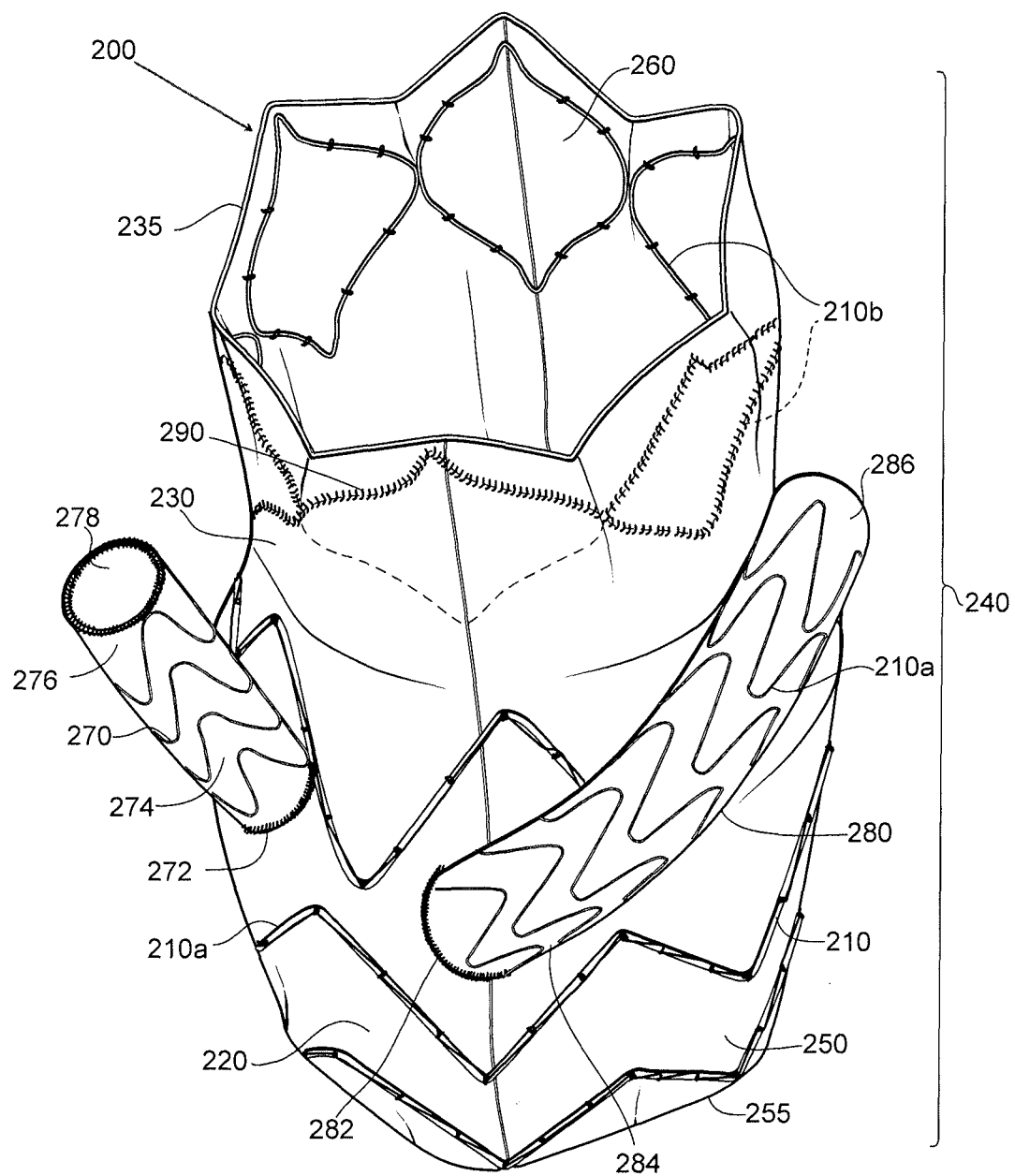
FIG. 5 is a side-bottom perspective view of an endograft having two external branches.

FIG. 5 illustrates a side-bottom perspective view of an alternative embodiment of an endograft 200 having two external coronary branches, and FIG. 6 illustrates a side view of endograft 200 with coronary connection stents 300 deployed. Endograft 200 comprises an expandable support structure 210 (including external Z-stents 210a and internal Z-stents 210b) and a graft material 220. Endograft 200 may comprise a main body 240 having a proximal region 230, a distal region 250, and a lumen 260 extending therebetween. The proximal region 230 may have a proximal opening 235 and the distal region 250 may have a distal opening 255, both of which may provide fluid access to the lumen 260 of the main body 240. The main body 240 may be generally tubular in shape, and have either a uniform or varying diameter along its length. For example, the proximal region 230 may have a smaller diameter than the distal region 250. The main body 240 may include a left coronary branch 270 and a right coronary branch 280, both primarily external to the main body 240, extending from a left coronary fenestration 272 and a right coronary fenestration 282, respectively. The left coronary branch 270 may have a proximal region 274, a distal region 276, and a lumen 278 therebetween. The right coronary branch 280 may have a proximal region 284, a distal region 286, and a lumen (not shown) therebetween.

The left and right coronary branches 270 and 280 may be configured to house tubular branch extensions such as coronary connection stents 300 that extend into the left coronary artery 20 and right coronary artery 18, respectively, forming a tromboning connection. The coronary connection stents 300 may comprise an expandable support structure 310 (e.g., laser-cut balloon expandable covered stents, laser-cut self-expandable covered stents, laser-cut balloon expandable segmented covered stents, external Z-stents, or internal Z-stents) and a biocompatible graft material 320, including a main body 340 having a proximal region 330, a distal region 350, and a lumen 360 extending therebetween. The proximal region 330 may have a proximal opening (not shown) and the distal region 350 may have a distal opening 355, both of which may provide fluid access to the lumen 360 of the main body 340.

Many elements of the endografts 200 and 300 are similar in structure and material to the endograft 100, for example, the expandable support structure 210 (including external Z-stents 210a and internal Z-stents 210b), graft material 220, main endograft body 240, helical right coronary branch 280, right coronary fenestration 282, and biocompatible stitching 290.

One difference between endograft 100 and endograft 200 is that a majority of left coronary branch 270 is located external to the main body 240. As shown in FIG. 5, the proximal region 274 (upstream) of the left coronary branch 270 may be attached to the fenestration 272 such that at least part of the left coronary branch 270 is outside the main body 240. Although the external left coronary branch 270 extends away from the main body 240 and towards the heart (proximally), in a fluid sense the blood flowing through the external left coronary branch 270 moves distally down the pressure gradient (downstream) towards the left coronary artery 20. The longitudinal axis of the left coronary branch 270 may be substantially parallel to the longitudinal axis of the left coronary artery 20. This may minimize potentially turbulent blood flow from the external left coronary branch 270 when it is fluidly coupled to the left coronary artery 20, for example through coronary connection stent 300.

In the embodiment of FIG. 5, only the proximal region 274 of the left coronary branch 270 is attached to the main body 240 (at fenestration 272), however, it may be preferable to attach the left coronary branch 270 to the main body 240 to limit the range of motion and pivoting.

The proximal regions 330 (upstream) of the coronary connection stents may sealingly engage with the distal regions 276 and 286 of the left coronary branch and right coronary branch, respectively. The seal may be formed via a compression fit, where in an expanded configuration the inner diameter of the distal regions 276 and 286 of the left and right coronary branches, respectively, are less than the outer diameter of the proximal regions 330 of the coronary connection stents. Additionally, the distal region 350 of the coronary connection stents 300 may sealingly engage with an inner surface of the surrounding blood vessels, for example, the right coronary artery 18 and left coronary artery 20.

Endograft 200 may be deployed using the methods outlined above. In addition to the advantages listed above, some advantages of an external left coronary branch 270 are that it would likely allow for easier access with wires, catheters, and sheaths as it would be less likely to snag on components within the branch (e.g., fenestration 272). Another advantage is that the length of the left coronary branch 270 would be shorter, meaning that blood would flow a shorter distance before reaching the left coronary artery 20, potentially leading to better perfusion. In addition, the main-body lumen 160 may be less obstructed by the internal branch 170 leading to less turbulent flow.

The embodiments described herein provide two non-limiting examples of endografts that are suitable for treating an array of medical conditions, and may be especially suited for treating an aortic aneurysm at or slightly above the aortic root 11. As will be appreciated, the main body 140 (or 240) may be positioned in the ascending aorta 14 slightly above the aortic root 11, while the left and right coronary branches 170 and 180 (or 270 and 280) are aligned with the left coronary artery 20 and right coronary artery 18, respectively. In both embodiments of endograft 100 and endograft 200, coronary connections stents 300 may extend into the left coronary artery 20 and right coronary artery 18.

Various additional modular components may be provided for the endograft 100 (or 200), for example, additional branch extensions or stents (not shown).

While references to treatment of an aortic aneurysm at or near the aortic root 11 may be explained as one example, it will be appreciated that endografts 100 and 200 can be positioned at other bodily locations to treat aneurysms or other conditions, using the system and methods described herein.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An endograft for placement in a vessel of a patient, comprising:
   a tubular main body portion having a proximal upstream end with a proximal opening, a distal downstream end with a distal opening, and a lumen extending therebetween;
   first and second fenestrations through a wall of the tubular main body portion that are in fluid communication with the lumen and are longitudinally offset from each other;
   a first branch having a first open end at the first fenestration and a second open end extending away from the first fenestration and a second branch having a first open end at the second fenestration and a second open end extending away from the second fenestration;
   wherein the first branch is helically curved around a partial circumference of the main body,
   wherein the second branch is straight relative to the first helical branch, and
   wherein the first and second branches are entirely longitudinally offset from one another and do not overlap, such that no portion of the first branch and the second branch lie in the same longitudinal portion of the main tubular body,
   wherein the first and second fenestrations are spaced apart less than 100 degrees relative to one another around a 360 degree perimeter of the main body, and wherein the second open ends of the first and second branches are between about 110 and about 250 degrees apart relative to one another around the perimeter of the main body.

2. An endograft for placement in a vessel of a patient, comprising:
   a tubular main body portion having a proximal upstream end with a proximal opening, a distal downstream end with a distal opening, and a lumen extending therebetween;
   first and second fenestrations through a wall of the tubular main body portion that are in fluid communication with the lumen and are longitudinally offset from each other;
   a first branch having a first open end at the first fenestration and a second open end extending away from the first fenestration and a second branch having a first open end at the second fenestration and a second open end extending away from the second fenestration;
   wherein the first branch is helically curved around a partial circumference of the main body,
   wherein the second branch is straight relative to the first helical branch, and
   wherein the first and second branches are entirely longitudinally offset from one another and do not overlap, such that no portion of the first branch and the second branch lie in the same longitudinal portion of the main tubular body,
   wherein the first open ends of the first and second branches are spaced apart less than 100 degrees relative to one another around a 360 degree perimeter of the main body, and wherein the second open ends of the first and second branches are between about 110 and about 250 degrees apart relative to one another around the perimeter of the main body.

3. An endograft for placement in a vessel of a patient, comprising:
   a tubular main body portion having a proximal end with a proximal opening, a distal end with a distal opening, and a lumen extending therebetween;
   first and second fenestrations through a wall of the tubular main body portion that are in fluid communication with the lumen;
   a first branch extending from the first fenestration and a second branch extending from the second fenestration, each of the first and second branches having an open end extending away from its fenestration;
   wherein the first branch is helically curved along a partial circumference of the main body,
   wherein the first and second fenestrations are spaced apart less than 100 degrees relative to one another around a 360 degree perimeter of the main body,
   wherein the distal downstream regions of the first and second branches are between about 110 and about 250 degrees apart relative to one another around the perimeter of the main body, and
   wherein the first branch second end extends away from the first fenestration in a first direction and the second branch end extends away from the second fenestration in a second direction opposite the first direction such that the first and second branches are entirely longitudinally non-overlapping.

4. The endograft of claim 1, further comprising at least one connection stent extending distally from the second ends of at least one of the first or second branches.

5. The endograft of claim 1, wherein the main body has a first side and a second side opposite the first side and the first and second fenestrations are located on the first side of the main body.

6. The endograft of claim 5, wherein the second ends of the first and second branches are located on opposite sides of the main body.

7. The endograft of claim 4, wherein a majority of the first branch is external to the main body, and wherein a majority of the second branch is internal to the main body.

8. The endograft of claim 3, wherein the second branch has a different shape from the first branch.

9. The endograft of claim 3, wherein the second branch is straight relative to the helical first branch and the second branch extends from the second fenestration toward the distal downstream end of the main body.

10. The endograft of claim 3, wherein a majority of the first branch is external to the main body and a majority of the second branch is internal to the main body.

11. The endograft of claim 3, wherein a majority of the first and second branches are external to the main body.

12. The endograft of claim 3, wherein the first and second fenestrations are spaced apart between approximately ten to fifty degrees relative to one another around the perimeter of the main body.

13. The endograft of claim 3, wherein the first and second fenestrations are spaced apart circumferentially relative to one another such that they lack circumferential overlap.

14. The endograft of claim 1,
wherein the proximal opening of the main body is closer to the second open end of the first branch than the first open end of the first branch, and
wherein the proximal opening of the main body is closer to the first open end of the second branch than it is to the second open end of the second branch.

15. The endograft of claim 1,
wherein the main body has a first side and second side opposite the first side and the first and second fenestrations, the first open end of the first branch and the second open end of the second branch are all on the same side of the main body and are all spaced within 100 degrees of each other around a 360 degree circumference of the main body, and
wherein the second open end of the first branch and the second open end of the second branch are spaced between about 110 and about 250 degrees apart from another around the circumference of the main body.

16. The endograft of claim 1,
wherein the first branch is attached to the first fenestration, and the second branch is attached to the second fenestration.

* * * * *